United States Patent [19]

Martin

[11] Patent Number: 4,931,089
[45] Date of Patent: Jun. 5, 1990

[54] HERBICIDAL OIL IN WATER COMPOSITIONS OF PENDIMETHALIN

[75] Inventor: Craig A. Martin, Pennington, N.J.

[73] Assignee: American Cyanamid Company, Stamford, Conn.

[21] Appl. No.: 234,062

[22] Filed: Aug. 18, 1988

Related U.S. Application Data

[63] Continuation of Ser. No. 7,066, Jan. 27, 1987, Pat. No. 4,810,279.

[51] Int. Cl.$^5$ .............................................. A01N 33/06
[52] U.S. Cl. .................................... 71/121; 71/DIG. 1
[58] Field of Search ............................ 71/DIG. 1, 121

[56] References Cited

U.S. PATENT DOCUMENTS

| | | | |
|---|---|---|---|
| 2,726,150 | 12/1955 | Wolter | 71/DIG. 1 |
| 3,067,254 | 12/1962 | Wilder | 71/121 |
| 4,077,795 | 3/1978 | Cooke et al. | 71/121 |
| 4,165,231 | 8/1979 | Lutz et al. | 71/121 |
| 4,174,960 | 11/1979 | Hendriksen | 71/121 |
| 4,541,860 | 10/1985 | Civilla et al. | 71/121 |
| 4,810,279 | 3/1989 | Martin | 71/121 |

FOREIGN PATENT DOCUMENTS 0978766 12/1975 Canada .

Primary Examiner—David B. Springer
Attorney, Agent, or Firm—Alice C. Brennan

[57] ABSTRACT

The present invention provides novel concentrated herbicidal oil in water emulsion compositions of pendimethalin and methods for their preparation.

6 Claims, No Drawings

HERBICIDAL OIL IN WATER COMPOSITIONS OF PENDIMETHALIN

This is a continuation of application, Ser. No. 007,066, filed Jan. 27, 1987, now U.S. Pat. No. 4,810,279.

BACKGROUND OF THE INVENTION

U.S. Pat. No. 4,174,960 describes concentrated aqueous emulsions containing on a weight basis 10% to 75% of one or more water insoluble herbicidal 2,6-dinitroaniline derivatives, 0% to 60% of a water immiscible solvent, 0.5% to 10% of an emulsifying agent and 15% to 70% of an aqueous solution containing at least 5% of an inorganic salt.

It is an object of this invention to provide concentrated aqueous emulsion compositions of N-(1-ethylpropyl)-2,6-dinitro-3,4-xylidine, (pendimethalin) and methods for their preparation.

SUMMARY OF THE INVENTION

The invention is herbicidal concentrated oil in water emulsion compositions comprising pendimethalin, a water immiscible solvent, alkylphenol polyethylene oxide condensate and ethylene oxide/propylene oxide block copolymer emulsifying agents and an anionic dispersant, and water, the emulsifying agents and dispersant being present in an amount resulting in a physically and chemically stable concentrated oil in water emulsion.

A preferred embodiment of the invention is herbicidal concentrated oil in water emulsion compositions comprising on a weight basis about 5% to 40% pendimethalin;
5% to 40% of a water immiscible solvent;
0.5% to 5.0% of an alkylphenol polyethylene oxide condensate;
0.5% to 5.0% of an ethylene oxide/propylene oxide block copolymer;
0% to 5.0% of an anionic dispersant; and sufficient water to total 100%.

Surprisingly it has been found that the compositions of this invention provide physically and chemically stable concentrated oil in water emulsions of pendimethalin which remain homogeneous and free flowing for extended periods of time and also retain their physical stability through repeated freezing and thawing cycles without settling, separating, coalescing, or precipitating insoluble solids, and which do not require the presence of inorganic salts in the aqueous phase. Uniquely, it has been found that the addition of inorganic salts to the aqueous phase is detrimental to the formation and stability of concentrated aqueous emulsion compositions of the present invention containing pendimethalin.

Concentrated aqueous emulsion combination compositions containing water soluble salts of herbicidal imidazolinyl acids and a herbicidal dinitroaniline compound are described in copending application for U.S. Letters Patent of C. Margin et al., Case 30,559 filed concurrently herewith.

The compositions of this invention comprise a continuous aqueous phase having dispersed therein an organic water immiscible solvent containing pendimethalin; having an average droplet size of less than 5 microns and preferably less than 2 microns; and the emulsifiers and dispersants described above.

A preferred group of ethylene oxide/propylene oxide block copolymers for use in the compositions of this invention are butyl-omega-hydroxypoly(oxypropylene) block polymer with poly(oxyethylene) having an average molecular weight in a range of 2,400 to 3,500, with alpha-butyl-omega-hydroxy-ethylene oxide propylene oxide block copolymers having an HLB of 12 and a viscosity at 25° C. of 2,000 CPS, (TOXIMUL ® 8320, Stepan Chemical Co) being a most preferred member of this class of emulsifiers.

Preferred alkylphenol polyethylene oxide condensates for use in the compositions of the invention are the nonylphenol ethoxylates, with nonylphenol ethoxylate (9 to 10 mols of ethylene oxide) (FLO MO ® 9N, DeSoto, Inc. Sellers Chemical Div.) being a most preferred member of this class of emulsifiers.

Preferred dispersing agents include the free acids of alkylphenol polyethylene oxide condensate phosphate esters, and dialkylphenol polyethylene oxide condensate phosphate esters, and the alkali metal salts especially the sodium salts of fatty acid taurides or fatty acid alkyltaurides. Examples of such fatty acids, which are frequently used in the form of mixtures, are straight-chain or branched saturated or mono- or polyunsaturated aliphatic carboxylic acids having about 10 to 20 carbon atoms, such as lauric acid, palmitic acid, stearic acid, myristic acid and especially oleic acid. The alkyl radical in fatty acid alkyltaurides is a lower alkyl radical with up to 4 C atoms, especially the methyl radical. Sodium N-methyl-N-oleoyltaurate (IGEPON ® T77, GAF Corporation), nonylphenol ethoxylate phosphate ester (6 mols EO) (FLO MO ® 6NP, DeSoto, Inc.), dinonylphenol ethoxylate phosphate ester (14 mols EO) (FLO MO ® 14 DNP, DeSoto, Inc.), being most preferred dispersing agents from these classes of compounds.

It is of course recognized that although it is not required in order to obtain stable compositions, that the concentrated emulsion compositions of the present invention may also optionally contain minor quantities (i.e., up to 10%) of adjuvants commonly employed in agricultural emulsion formulations such as antifoaming agents, biocides, antifreezing agents, rheological control agents, coloring agents and the like, in order to accommodate cultural agricultural practices and preferences and climatic variations.

Organic solvents suitable for use as the organic phase in the compositions of this invention include hydrocarbon, aromatic hydrocarbon, chlorinated hydrocarbon and chlorinated aromatic hydrocarbon solvents and mixtures thereof; such as toluene, xylenes, polynuclear aromatic hydrocarbons such as naphthalenes and alkylnaphthalenes and mixtures thereof, many of which are available from the fractionation of crude oil and in general have distillation ranges in the temperature range of about 118° to 305° C. and are commercially available under a variety of tradenames; mono or polychloroalkanes such as dichloroethane, and mono or polychlorobenzene and toluenes.

The compositions of the invention may readily be prepared by high shear mixing in a temperature range of about 20° C. to 75° C. of a mixture comprising the organic phase containing pendimethalin which may also contain a portion or all of the emulsifying agent(s) with an aqueous phase which may also contain the dispersing agent, and/or a portion or all of the emulsifying sufficient period of time to obtain an emulsion having an average droplet size of 5 microns or less and preferably less than 2 microns.

In accordance with the above procedure, compositions of the invention may be prepared by A. Preparing an organic phase by
1. adding the desired quantity of pendimethalin to a sufficient quantity of the organic solvent;
2. if desired, adding a portion or all of the emulsifying agent(s);
3. agitating until all the solids dissolve;
4. optionally clarifying the organic phase by filtration.

B. Preparing an aqueous phase by adding if desired the dispersing agent and a portion or all of the emulsifying agent(s).

C. Preparing the concentrated emulsion by combining the aqueous phase and the organic phase and subjecting the mixture to high shear mixing and continue mixing until a homogeneous emulsion having the desired droplet size is obtained, and package the product.

In general, the above procedure has been found suitable for the preparation of the stable concentrated emulsions of this invention both by adding the aqueous phase to the organic phase or by adding the organic phase to the aqueous phase and has also yielded equally good results when the emulsifying agents reside in either the organic phase or the aqueous phase.

The present invention is further illustrated by the following non-limiting examples.

EXAMPLES 1-5

Preparation of Concentrated Aqueous Emulsion of Pendimethalin

An aqueous solution of the emulsifying agents and dispersing agents, listed in Table I below, at 60° C. is combined with a solution of pendimethalin in the water immiscible solvents listed in Table I below.

The resulting mixture is subjected to high shear mixing for 10 minutes at 60° C. and the mixing continued thereafter until the emulsion has cooled to 20° C., after which the composition is collected. Utilizing the above procedure yields the stable concentrated aqueous emulsions listed in Table II below.

TABLE I

1. Emulsifying and Dispersing Agent
    a. nonylphenol ethoxylate (9 to 10 mols of ethylene oxide)
    b. alpha-butyl-omega-hydroxy-ethylene oxide propylene oxide block copolymer, HLB 12, viscosity @ 25° C.: 2000 CPS
    c. sodium N-methyl-N-oleoyltaurate
    d. dinonylphenol ethoxylate phosphate ester (14 mols EO)
    e. nonylphenol ethoxylate phosphate ester (6 mols EO)
2. Organic Solvent
    a. monochlorobenzene
    b. aromatic hydrocarbon mixture (C$_8$ to C$_9$ aromatics, distillation range 155°–173° C.; AROMATIC® 100, Exxon)
3. Water

TABLE II

| Pendi-methalin % w/w | Organic solvent/ % w/w | % Emulsifying and dispersing agent/ | | | Water |
|---|---|---|---|---|---|
| | | % w/w | % w/w | % w/w | |
| 34.9 | 2a/30.0 | 1a/2.0 | 1b/2.0 | 1c/2.0 | 29.1 |
| 25.0 | 2a/29.9 | 1a/2.0 | 1b/2.1 | 1c/2.0 | 38.9 |
| 20.0 | 2a/30.0 | 1a/2.0 | 1b/2.0 | 1c/2.0 | 44.0 |
| 30.0 | 2b/29.9 | 1a/2.0 | 1b/2.2 | 1d/1.9 | 34.0 |
| 30.1 | 2b/30.0 | 1a/2.0 | 1b/2.0 | 1e/2.0 | 33.9 |

EXAMPLE 6

Attempt to Prepare a Concentrated Aqueous Emulsion Containing Pendimethalin with Sodium Chloride in the Aqueous Phase An aqueous phase comprising on a weight basis 5.4% of sodium chloride, 2.0% sodium N-methyl-N-oleoyltaurate, and 35.4% of water is combined with an organic phase comprising on a weight basis 2.0% of nonylphenol ethoxylate (9–10 mols of ethylene oxide), 2.0% of alpha-butyl-omega-hydroxy-ethylene oxide propylene oxide block copolymer having an HLB of 12 and viscosity @ 25° C. of 2000 CPS; 23.5% of pendimethalin and 30.0% monochlorobenzene and the resulting mixture is subjected to high shear mixing for 15 minutes. Upon completion of the mixing, the mixture separates immediately upon standing indicating that no emulsion is formed.

What is claimed is:

1. A herbicidal concentrated oil in water emulsion composition consisting essentially of, on a weight basis, about 5% to 40% pendimethalin; 5% to 40% of a water immiscible solvent; 0.5% to 5.0% of an alkylphenol polyethylene oxide condensate; 0.5% to 5.0% of an ethylene oxide/propylene oxide block copolymer; 0% to 5.0% of an anionic dispersant; and sufficient water to total 100%; wherein said water immiscible solvent consists essentially of xylene or an aromatic hydrocarbon mixture having a distillation range in a temperature range of about 183° C. to about 305° C.

2. The composition according to claim 1 wherein the alkylphenol polyethylene oxide condensate is a nonylphenol ethoxylate with 9 to 10 mols of ethylene oxide; the ethylene oxide/propylene oxide block copolymer is a butyl-omega-hydroxypoly(oxypropylene)block copolymer with poly(oxyethylene) having a molecular weight in a range of 2,400 to 3,500; the anionic dispersing agent is an alkali metal salt of fatty acid tauride or fatty acid alkyltauride or a free acid of an alkylphenol ethoxylate phosphate ester or a dialkylphenol ethoxylate phosphate ester.

3. The composition according to claim 2 wherein the dispersed organic phase has an average droplet size of less than 2 microns.

4. The composition according to claim 3 wherein the composition contains alpha-butyl-omega-hydroxy-ethylene oxide propylene oxide block copolymer having an HLB of 12 and a viscosity at 25° C. of 2,000 CPS, nonylphenol ethoxylate (9 to 10 mols of ethylene oxide), and the dispersing agent is sodium N-methyl-N-oleoyltaurate or nonylphenol ethoxylate phosphate ester (6 mols EO), or dinonylphenol ethoxylate phosphate ester (14 mols EO).

5. The composition according to claim 4 consisting essentially of, on a weight basis, 20% to 35% pendimethalin; 25% to 35% water immiscible solvent; 1.5% to 2.5% alpha-butyl-omega-hydroxyethylene oxide propylene oxide block copolymer having an HLB of 12 and a viscosity at 25° C. of 2,000 CPS; 1.5% to 2.5% nonylphenol ethoxylate (9 to 10 mols of ethylene oxide); 1.5% to 2.5% dispersing agent; and a sufficient amount of water to total 100%.

6. A herbicidal concentrated oil in water emulsion composition consisting essentially of 5% to 40% pendimethalin, 5% to 40% of a water immiscible solvent, alkylphenol polyethylene oxide condensate and ethylene oxide/propylene oxide block copolymer emulsifying agents, an anionic dispersant, and water, the emulsifying agents and dispersant being present in an amount resulting in a physically and chemically stable concentrated oil in water emulsion; wherein said water immiscible solvent consists essentially of xylene or an aromatic hydrocarbon mixture having a distillation range in a temperature range of about 183° C. to about 305° C.

* * * * *